United States Patent [19]
Chamberlain

[11] 3,954,406
[45] May 4, 1976

[54] LOAD PREHEATING AND STERILIZING METHOD

[75] Inventor: Robert E. Chamberlain, Erie, Pa.

[73] Assignee: American Sterilizer Company, Erie, Pa.

[22] Filed: Mar. 14, 1972

[21] Appl. No.: 234,508

Related U.S. Application Data

[63] Continuation-in-part of Ser. No. 852,608, Aug. 25, 1969, abandoned.

[52] U.S. Cl. .................................. 21/57; 21/58; 21/DIG. 4
[51] Int. Cl.² .................................... A61L 13/00
[58] Field of Search ........................ 21/56–58, 21/DIG. 4

[56] References Cited
UNITED STATES PATENTS

| | | | |
|---|---|---|---|
| 1,955,289 | 4/1934 | Greenheld | 21/56 UX |
| 2,080,179 | 5/1937 | Merriam et al. | 21/58 |
| 2,536,115 | 1/1951 | Wilbur | 21/56 UX |
| 2,868,616 | 1/1959 | Poitras | 21/56 |
| 3,035,886 | 5/1962 | Hickey | 21/57 |
| 3,068,064 | 12/1962 | McDonald | 21/58 |
| 3,093,449 | 6/1963 | Kotarski et al. | 21/56 X |
| 3,598,516 | 8/1971 | Shull et al. | 21/57 |
| 3,598,517 | 8/1971 | Beecher | 21/58 |

Primary Examiner—Barry S. Richman

[57] ABSTRACT

An apparatus and method for preheating a load of goods sealed in a semi-permeable package and subsequently sterilizing the goods in a microbiocidal gas cycle wherein the heat is obtained from the condensate of low pressure steam, which is used to heat the goods. The system operates at or about atmospheric pressure with steam mixed with air to obtain the partial pressure of steam equivalent to the desired temperature, the air being present in the preheating step to prevent the package from rupturing due to the creation of an overpressure therein. The air is heated slightly above the desired load temperature. The air may be heated by absorbing the superheat from the steam as the line pressure is reduced.

4 Claims, 1 Drawing Figure

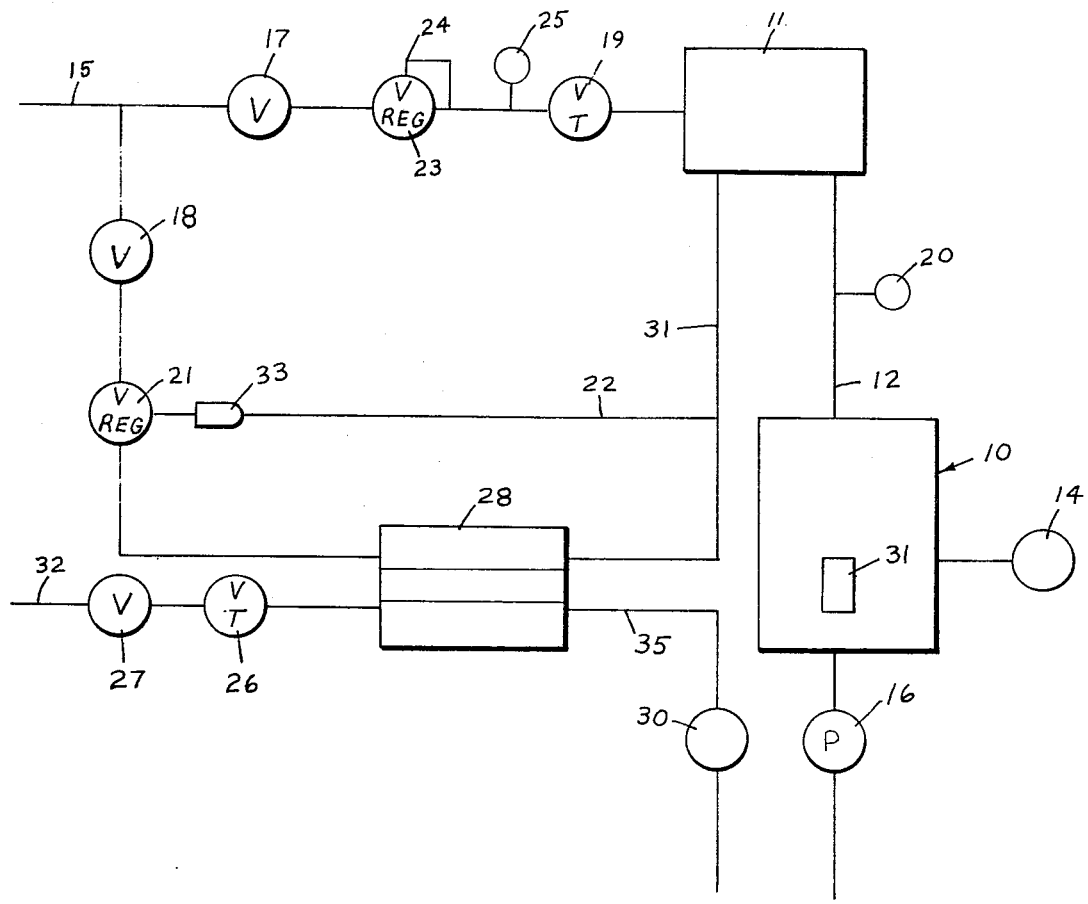

3,954,406

LOAD PREHEATING AND STERILIZING METHOD

CROSS-REFERENCE TO RELATED APPLICATION

This application is a continuation-in-part of patent application, Ser. No. 852,608, filed Aug. 25, 1969 and now abandoned.

STATEMENT OF INVENTION

This invention relates to sterilizers, and more particularly, to a method and apparatus for heating a load of goods to be sterilized, in a gas cycle in combination with said gas cycle.

REFERENCE TO RELATED APPLICATIONS

The heating means and method disclosed herein are suitable for use in combination with a gas sterilizing cycle, such as disclosed in patent application, Ser. No. 827,471, filed in the name of Donald J. Beecher and assigned to applicant's assignee, and which issued as U.S. Pat. No. 3,598,517 on Aug. 10, 1971.

The said patent discloses a method for sterilizing articles that are packaged in materials made of semipermeable material.

GENERAL DESCRIPTION OF PROCESS

In a sterilizing cycle utilizing a microbicidal gas, such as ethylene oxide, the length of time necessary to carry out a satisfactory sterilizing cycle is dependent on the temperature in which the cycle is carried out. It has been determined that a temperature of 130° F. is a suitable temperature for sterilizing. If the cycle is carried out at temperatures below this, the time for sterilizing increases notably.

The sterilizing of such articles involves items which cannot be subjected to vacuum. It has been found that the items in standard heated wall sterilizers, heat up very slowly. Many times the articles do not reach the desired or allowed temperature by the end of the extended exposure periods. The present system will raise the load temperatures to that desired in a reasonable time, approximately thirty minutes. This system operates at atmospheric pressure and the source of heat is obtained from the condensation of low pressure steam mixed with air in the required proportions to obtain a partial pressure steam equivalent to the desired temperature.

The air mixed with the steam in chamber 11 should be heated to slightly above the desired load temperature such that it will not condense any of the steam in the process. If steam is at approximate saturated conditions, the control of load temperature is simplified. Some of the heat used to raise the air temperature can be obtained from the steam in absorbing the superheat available when the line pressure steam is reduced to a low value.

OBJECTS OF THE INVENTION

It is an object of the invention to provide an improved means for heating goods.

Another object of the invention is to provide an improved heating means for use in combination with a sterilizing cycle.

Another object of the invention is to provide an improved means for heating goods prior to the introduction of sterilizing gas in a gas sterilizing cycle.

Another object of the invention is to provide a sterilizing cycle which is simple, efficient and can be carried out with a minimum of equipment.

DESCRIPTION OF THE DRAWING

The drawing shows a general schematic diagram of an apparatus for carrying out the invention.

DETAILED DESCRIPTION OF THE DRAWING

The schematic drawing disclosed herein shows the piping and control apparatus for controlling the steam and gas to heat a load to the desired temperature. A temperature of 130° F. has been considered to be a suitable temperature for carrying out the gas sterilizing cycle. The pressure of saturated steam at this temperature is 115 mm. Hg. Abs. This value can be obtained from any steam table.

In the drawing, a sterilizing chamber 10 is shown having an article 31 shown schematically therein which may be considered to be an article packaged in a semipermeable membrane, such as polyethylene.

In order to adjust the pressure regulating valve 23, the throttling valve 19, the temperature control valve 21, and the throttling valve 26 so that the machine can be shut down and started up by opening and closing valves 17 and 27, the following procedure may be followed.

First, the vacuum pump 16 is started and it runs continuously when the machine is operating.

Valves 17 and 18 are closed and the valve 27 is opened and valve 26 adjusted until the pressure read on gauge 14 is equal to 1 atmosphere minus the saturated steam pressure at the temperature to which the load is to be heated, i.e. 130° F., that is, the throttling valve 26 is adjusted until the pressure in the chamber reads 760 mm. Hg. Abs. minus 115 mm. Hg. Abs. or 645 mm. Hg. Abs. (25.4 in. Hg. Abs.).

The operator then opens valve 18 and sets the temperature modulating valve 21 by adjusting the control thereon 33 to control the temperature in line 31 at approximately 100° F. The control element 33 senses the temperature in line 31 through the line 22. The operator then opens valve 19 and adjusts it so that the pressure in chamber 10 is read on gauge 14 reaches atmospheric. The temperature indicated at 20 should be approximately 130° F. at this point (that is, slightly above the saturated temperature to insure dry steam but little superheat).

If the temperature is too high, a lower setting on the air temperature control 21 can be made. If the temperature is too low, the temperature control 33 can be raised. When the temperature is correct, valves 17, 18 and 27 may be used to shut down and start up the system.

Referring now to the system shown, the chamber 10 may be a suitable autoclave structure with a vacuum pump 16 connected to the lower part of it and a suitable gauge 14. The mixing chamber 11 is connected to the autoclave by line 12. The mixing chamber has line 31 connected to it and, likewise, line 15. An air supply is connected through line 32 which may be controlled by shut off valve 27 and throttling valve 26 and connected through the heat exchanger 28 to line 31. The steam at approximately 30 psi will be connected to line 15 and through shut off valve 17, regulating valve 23 and throttling valve 19 to the mixer 11. The pressure at the regulator is measured by gauge 25. Steam from line 15 passes through throttling valve 18 and temperature control valve 21 through the heat exchanger 28 to the drain 35. The temperature of the air in line 31 is controlled by the amount of steam passing through temperature control valve 21 through the heat exchanger 28.

The load of goods indicated at 31 can be heated prior to admission of gas to the chamber in accordance with the balanced pressure cycle referred to in U.S. Pat. No. 3,598,517.

From the above it will be seen that the partial pressure of steam in the chamber 10 plus the partial pressure of air total so that the pressure in the chamber around the article 31 is equal to atmospheric. The pump 16 runs at all times when the cycle is operating.

The embodiments of the invention in which an exclusive property or privelege is claimed are defined as follows:

1. In combination, a process for preheating to a predetermined temperature an article to be sterilized in a sealed, semi-permeable package that would be damaged if exposed to vacuum and which will not tolerate temperatures above the temperature of saturated steam at atmospheric pressure followed by the introduction of a microbiocidal sterilizing gas comprising
   a. loading said chamber with said article to be sterilized,
   b. evacuating said chamber to a selected pressure level and continuing to evacuate said chamber and simultaneously
   c. introducing air to said chamber at a pressure that will maintain a pressure in said chamber equal to atmospheric pressure less the saturated steam pressure at said desired temperature,
   d. continuing said introduction of air and simultaneously introducing steam to said chamber at said saturated pressure whereby said chamber is maintained at said selected temperature, continuing said evacuation of said air and said introduction of said steam to said chamber for a period of time sufficient to heat said article to said desired temperature,
   e. and then introducing a microbiocidal sterilizing gas to said chamber to sterilize said article.

2. The process recited in claim 1 wherein said desired temperature is approximately 130° Fahrenheit.

3. The process recited in claim 1 wherein said steam and said air are mixed before admitting them to said chamber.

4. The process of claim 1 wherein said air is preheated by said steam.

* * * * *